US012239952B2

(12) United States Patent
Alroaithi et al.

(10) Patent No.: US 12,239,952 B2
(45) Date of Patent: Mar. 4, 2025

(54) SYSTEMS AND METHODS FOR DRYING COMPOUNDS (71) Applicant: Saudi Aramco Technologies Company, Dhahran (SA)

(72) Inventors: Mohammad S. Alroaithi, Thuwal (SA); Hussain M. Yami, Thuwal (SA); Ali M. Albarakati, Thuwal (SA); Wei Xu, Thuwal (SA)

(73) Assignee: SAUDI ARAMCO TECHNOLOGIES COMPANY, Dhahran (SA)

( * ) Notice: Subject to any disclaimer, the term of this patent is extended or adjusted under 35 U.S.C. 154(b) by 0 days.

(21) Appl. No.: 17/574,830

(22) Filed: Jan. 13, 2022

(65) Prior Publication Data
US 2022/0226800 A1 Jul. 21, 2022

Related U.S. Application Data (60) Provisional application No. 63/137,979, filed on Jan. 15, 2021.

(51) Int. Cl.
*B01J 20/18* (2006.01)
*C01B 39/46* (2006.01)
*C07C 41/36* (2006.01)

(52) U.S. Cl.
CPC ............... *B01J 20/18* (2013.01); *C01B 39/46* (2013.01); *C07C 41/36* (2013.01); *C01P 2002/34* (2013.01); *C01P 2006/14* (2013.01)

(58) Field of Classification Search
None
See application file for complete search history.

(56) References Cited

U.S. PATENT DOCUMENTS

| | | |
|---|---|---|
| 2009/0260754 A1 | 10/2009 | Te Poel |
| 2011/0245424 A1 | 10/2011 | Jeong et al. |
| 2018/0215685 A1* | 8/2018 | Paek .............. C07C 5/367 |
| 2020/0368718 A1* | 11/2020 | Guo .............. B01D 53/02 |

FOREIGN PATENT DOCUMENTS

| | | | |
|---|---|---|---|
| CN | 1597720 | * | 3/2005 |
| CN | 104 829 430 A | | 8/2015 |
| CN | 104829430 | * | 8/2015 |
| CN | 105255348 | * | 1/2016 |
| CN | 109280469 | * | 1/2019 |
| CN | 110605032 | * | 12/2019 |
| CN | 11632575 | * | 9/2020 |
| DE | 197 16 413 A1 | | 10/1998 |
| WO | WO-2008/052841 A1 | | 5/2008 |
| WO | WO-2010/028362 A1 | | 3/2010 |
| WO | WO-2012/071505 A1 | | 5/2012 |
| WO | WO-2019/032524 A1 | | 2/2019 |
| WO | WO-2020/028606 A1 | | 2/2020 |
| WO | WO-2020/068796 A9 | | 7/2020 |
| WO | WO-2021/262845 A1 | | 12/2021 |
| WO | WO-2022/153213 A1 | | 7/2022 |

OTHER PUBLICATIONS

Cyriac A., et al., Preparation of flame-retarding poly(propylene carbonate), Green Chem. 13:3469-3475 (2011).
Ignatov, V.N., et al., Methods of investigation molecular sieve drying of polyethylene glycols, Polymer Science USSR, 29(11):2709-2711 (1987).
International Search Report for PCT/IB2022/050266, 7 pages (Jun. 1, 2022).

* cited by examiner

*Primary Examiner* — Sheng H Davis
(74) *Attorney, Agent, or Firm* — Osha Bergman Watanabe & Burton LLP (57) ABSTRACT

This application relates to methods and systems for drying polyol starters, as well as reaction mixtures including such polyol starters, and the preparation of polymers derived from such polyol starters. In some embodiments, the present invention encompasses methods of drying a polyol initiator compound, the method including the step of contacting a composition comprising a polyol initiator compound with one or more molecular sieves.

7 Claims, 3 Drawing Sheets

SYSTEMS AND METHODS FOR DRYING COMPOUNDS

CROSS-REFERENCE TO RELATED APPLICATIONS

This application claims priority to U.S. Provisional Patent Application No. 63/137,979, filed Jan. 15, 2021, the entire of which is hereby incorporated by reference.

FIELD OF INVENTION

This invention pertains to systems and methods for drying compounds. More particularly, the invention pertains to methods and systems for drying polyol starters, as well as reaction mixtures comprising such polyol starters, and the preparation of polymers derived from such polyol starters.

BACKGROUND

Certain polymers, e.g., polyols, may be prepared with an initiator compound, whereby homogenous chain-growth polymerization initiates from each functional end group of the initiator compound. However, initiator compounds can contain high amounts of water, which lengthens the catalyst induction time for polymerization and potentially leads to catalyst deactivation. Therefore, the presence of water in initiator compounds (e.g., polyol initiator compounds) must be eliminated or reduced to improve polymerization reactions.

SUMMARY OF INVENTION

Polyols are used in combination with isocyanates in the production of polyurethanes. For example, in certain applications, polyether polyols, polyester polyols, and polycarbonate polyols are used in polyurethane compositions. In one aspect, polyols (e.g., polyether polyols, polyester polyols, or polycarbonate polyols) are derived from a polyol initiator compound whereby homogenous chain-growth polymerization initiates from each functional end group of the polyol initiator compound.

A catalyst is typically used in the polymerization of such polyols, and these catalysts may be sensitive to moisture (water). The presence of water can lengthen reaction induction time and also may deactivate the catalyst. Therefore, the presence of water within a polymerization reaction mixture (e.g., using a polyol initiator compound contaminated with water) must be eliminated or reduced (e.g., less than 200 ppm, or less than 100 ppm) for optimal polymerization of such polyols.

However, moisture reduction in this context can be challenging since polyol initiator compounds often display high viscosities (e.g., 75 cP at 25° C.), making removal of water more difficult. For example, processes to "blow away" water with hot $N_2$ gas have been disclosed, but these processes are energy consuming and waste large amounts of $N_2$. Thus, effective and less energy-consuming processes for removing water from polyol initiator compounds are highly desired.

Molecular sieves are often used to dry gases and liquids. Molecule sieves are advantageous because, unlike blowing $N_2$ gas, molecular sieves can be regenerated and employed in a continuous process, which are particularly beneficial when drying gases and liquids on a large-scale. However, due to the high viscosities of some polyol initiator compounds, the moisture diffusion rate at room temperatures is very slow and leads to a lengthy process to reduce the moisture to desired levels. In one aspect, the present invention encompasses the recognition that, at certain temperatures, the viscosities of certain polyol initiator compounds are reduced dramatically.

In one aspect, the present invention encompasses methods of drying (e.g., removing water from) a polyol initiator compound, the method comprising the step of contacting a composition comprising a polyol initiator compound with one or more molecular sieves. In some embodiments, molecular sieves are maintained at a temperature between about 50° C. and about 100° C. while in contact with the polyol initiator compound. In some embodiments, a composition comprising a polyol initiator compound flows through a vessel containing molecular sieves at a flow rate of about 0.5 to about 2.5 mL/min.

In another aspect, the present invention encompasses compositions comprising a polyol initiator compound obtained by or obtainable by the methods described above and herein (e.g., with less than 100 ppm water).

In another aspect, the present invention encompasses mixtures comprising a polyol initiator compound obtained by or obtainable by the methods described above and herein (e.g., with less than 100 ppm water) and a polymerization catalyst.

In another aspect, the present invention encompasses systems for drying a polyol initiator compound, the system comprising:
 a vessel comprising one or more molecular sieve beads; and
 a polyol initiator input subsystem connected to the vessel, wherein the polyol initiator flows into the vessel through the polyol initiator input subsystem.

In some embodiments, the vessel is maintained at a temperature between about 50° C. and about 100° C. In some embodiments, the composition flows through the vessel at a flow rate of about 0.5 to about 2.5 mL/min.

BRIEF DESCRIPTION OF THE DRAWING

Drawings are presented herein for illustration purposes, not for limitation. The foregoing and other objects, aspects, features, and advantages of the disclosure will become more apparent and may be better understood by referring to the following description taken in conjunction with the accompanying drawings, in which.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain molecules of the present invention can comprise one or more asymmetric centers, and thus can exist in various stereoisomeric forms, e.g., enantiomers and/or diastereomers. Thus, inventive molecules and compositions thereof may be in the form of an individual enantiomer, diastereomer or geometric isomer, or may be in the form of a mixture of stereoisomers. In certain embodiments, the molecules of the invention are enantiopure molecules. In certain embodiments, mixtures of enantiomers or diastereomers are provided.

Certain molecules described herein may have one or more double bonds that can exist as either the Z or E isomer, unless otherwise indicated. The invention additionally encompasses the molecules as individual isomers substantially free of other isomers and alternatively, as mixtures of various isomers, e.g., racemic mixtures of enantiomers. In addition to the above-mentioned molecules per se, this invention also encompasses compositions comprising one or more molecules.

The term "polyol initiator compound," as used herein, refers to a polyfunctional compound having two or more sites from which polymerization can occur

DETAILED DESCRIPTION OF CERTAIN EMBODIMENTS

I. Methods

In certain embodiments, the present invention encompasses methods of drying a compound (e.g., a diol, triol, polyhydric alcohol, hydroxyl acid), the method comprising the step of contacting a composition comprising the compound with one or more molecular sieves.

In certain embodiments, the present invention encompasses methods of drying (e.g., removing water from) a polyol initiator compound, the method comprising the step of contacting a composition comprising a polyol initiator compound with one or more molecular sieves.

A. Molecular Sieves

In some embodiments, a molecular sieve is spherical (i.e., "beads"). In some embodiments, a molecular sieve is cylindrical.

In some embodiments, a molecular sieve has an average pore size between about 1 angstrom and about 6 angstroms. In some embodiments, a molecular sieve has an average pore size between about 2 angstroms and about 5 angstroms. In some embodiments, a molecular sieve has an average pore size between about 3 angstroms and about 5 angstroms. In some embodiments, a molecular sieve has an average pore size between about 3 angstroms and about 4 angstroms. In some embodiments, a molecular sieve has an average pore size between about 4 angstroms and about 5 angstroms. In some embodiments, a molecular sieve has an average pore size of about 3 angstroms. In some embodiments, a molecular sieve has an average pore size of about 4 angstroms. In some embodiments, a molecular sieve has an average pore size of about 5 angstroms.

In some embodiments, a porosity of a molecular sieve is within a range of about 10% to about 90%. In some embodiments, a porosity of a molecular sieve is within a range of about 10% to about 50%. In some embodiments, a porosity of a molecular sieve is within a range of about 30% to about 70%. In some embodiments, a porosity of a molecular sieve is within a range of about 50% to about 90%. In some embodiments, a porosity of a molecular sieve is within a range of about 10% to about 20%. In some embodiments, a porosity of a molecular sieve is within a range of about 20% to about 30%. In some embodiments, a porosity of a molecular sieve is within a range of about 30% to about 40%. In some embodiments, a porosity of a molecular sieve is within a range of about 50% to about 60%. In some embodiments, a porosity of a molecular sieve is within a range of about 60% to about 70%. In some embodiments, a porosity of a molecular sieve is within a range of about 70% to about 80%. In some embodiments, a porosity of a molecular sieve is within a range of about 80% to about 90%.

In some embodiments, a molecular sieve is an aluminosilicate. In some embodiments, a molecular sieve is a sodium, potassium, or calcium aluminosilicate. In some embodiments, a molecular sieve is a sodium aluminosilicate. In some embodiments, a molecular sieve is a potassium aluminosilicate. In some embodiments, a molecular sieve is a calcium aluminosilicate. In some embodiments, a molecular sieve is a crystalline aluminosilicate. In some embodiments, a molecular sieve is a crystalline sodium, potassium, or calcium aluminosilicate. In some embodiments, a molecular sieve is a crystalline sodium aluminosilicate. In some embodiments, a molecular sieve is a crystalline potassium aluminosilicate. In some embodiments, a molecular sieve is a crystalline calcium aluminosilicate.

In some embodiments, a molecular sieve used in accordance with provided methods and systems is activated. For example, in some embodiments, a molecular sieve is activated by raising its temperature for a period of time. The skilled person will be aware of techniques for applying heat to molecular sieves, including, by way of non-limiting example, heating elements, ovens, and microwaves, optionally with reduced pressure and/or inert gas flow. In some embodiments, a molecular sieve is activated by maintaining its temperature above about 100° C. In some embodiments, a molecular sieve is activated by maintaining its temperature above about 200° C. In some embodiments, a molecular sieve is activated by maintaining its temperature above about 250° C. In some embodiments, a molecular sieve is activated by maintaining its temperature above about 280° C. In some embodiments, a molecular sieve is activated by maintaining its temperature above about 300° C. In some embodiments, a molecular sieve is activated by maintaining its temperature between about 100° C. and about 400° C. In some embodiments, a molecular sieve is activated by maintaining its temperature between about 200° C. and about 400° C. In some embodiments, a molecular sieve is activated by maintaining its temperature between about 200° C. and about 350° C. In some embodiments, a molecular sieve is activated by maintaining its temperature between about 250° C. and about 350° C. In some embodiments, a molecular sieve is activated by maintaining its temperature between about 280° C. and about 300° C.

In some embodiments, a molecular sieve is activated by maintaining its temperature at any of the temperatures listed above for at least 1 hr. In some embodiments, a molecular sieve is activated by maintaining its temperature at any of the temperatures listed above for at least 2 hrs. In some embodiments, a molecular sieve is activated by maintaining its temperature at any of the temperatures listed above for at least 3 hrs. In some embodiments, a molecular sieve is activated by maintaining its temperature at any of the temperatures listed above for between about 1 hr and about 5 hrs. In some embodiments, a molecular sieve is activated by maintaining its temperature at any of the temperatures listed above for between about 2 hr and about 4 hrs. In some embodiments, a molecular sieve is activated by maintaining its temperature at any of the temperatures listed above for between about 2.5 hr and about 3.5 hrs. In some embodiments, a molecular sieve is activated by maintaining its temperature at any of the temperatures listed above for between about 1 hr, 2, hrs, 3, hrs, 4 hr, or 5 hrs.

In some embodiments, a molecular sieve is activated by maintaining its temperature above about 250° C. for about 3 hrs. In some embodiments, a molecular sieve is activated by maintaining its temperature between about 280° C. and about 300° C. for about 3 hrs.

In one aspect, a molecular sieve is maintained at a temperature while in contact with a polyol initiator compound. In some embodiments, a molecular sieve is maintained at a temperature between about 20° C. and about 200° C. while in contact with a polyol initiator compound. In some embodiments, a molecular sieve is maintained at a temperature between about 30° C. and about 150° C. while in contact with a polyol initiator compound. In some embodiments, a molecular sieve is maintained at a temperature between about 30° C. and about 120° C. while in contact with a polyol initiator compound. In some embodiments, a molecular sieve is maintained at a temperature between about 40° C. and about 100° C. while in contact with a polyol initiator compound. In some embodiments, a molecular sieve is maintained at a temperature between about 50° C. and about 100° C. while in contact with a polyol initiator compound. In some embodiments, a molecular sieve is maintained at a temperature between about 75° C. and about 100° C. while in contact with a polyol initiator compound. In some embodiments, a molecular sieve is maintained at a temperature between about 50° C. and about 75° C. while in contact with a polyol initiator compound. In some embodiments, a molecular sieve is maintained at a temperature between about 100° C. and about 200° C. while in contact with a polyol initiator compound. In some embodiments, a molecular sieve is maintained at a temperature between about 100° C. and about 150° C. while in contact with a polyol initiator compound.

B. Polyol Initiator Compounds

In some embodiments, a polyol initiator compound is a compound suitable to initiate polymerization of polyether polyols, polyester polyols, or polycarbonate polyols. In some embodiments, a polyol initiator compound is a compound suitable to initiate polymerization of polyether polyols. In some embodiments, a polyol initiator compound is a compound suitable to initiate polymerization of polyester polyols. In some embodiments, a polyol initiator compound is a compound suitable to initiate polymerization of polycarbonate polyols.

In some embodiments, a polyol initiator compound is a compound having two or more sites from which epoxide/$CO_2$ copolymerization can occur, for example, as published in PCT application WO 2010/028362, US 2011/0245424, or Green Chem. 2011, 13, 3469-3475.

In some embodiments, a polyol initiator compound is a dihydric alcohol. In some embodiments, a polyol initiator compound is a $C_{2-40}$ diol. In some embodiments, a polyol initiator compound is selected from the group consisting of 1,2-ethanediol, 1,2-propanediol, 1,3-propanediol, 1,2-butanediol, 1,3-butanediol, 1,4-butanediol, 1,5-pentanediol, 2,2-dimethylpropane-1,3-diol, 2-butyl-2-ethylpropane-1,3-diol, 2-methyl-2,4-pentane diol, 2-ethyl-1,3-hexane diol, 2-methyl-1,3-propane diol, 1,5-hexanediol, 1,6-hexanediol, 1,8-octanediol, 1,10-decanediol, 1,12-dodecanediol, 2,2,4,4-tetramethylcyclobutane-1,3-diol, 1,3-cyclopentanediol, 1,2-cyclohexanediol, 1,3-cyclohexanediol, 1,4-cyclohexanediol, 1,2-cyclohexanedimethanol, 1,3-cyclohexanedimethanol, 1,4-cyclohexanedimethanol, 1,4-cyclohexanediethanol, isosorbide, glycerol monoesters, glycerol monoethers, trimethylolpropane monoesters, trimethylolpropane monoethers, pentaerythritol diesters, pentaerythritol diethers, and alkoxylated derivatives of any of these.

In some embodiments, a polyol initiator compound is diethylene glycol, triethylene glycol, tetraethylene glycol, higher poly(ethylene glycol), such as those having number average molecular weights of from 220 to about 2000 g/mol, dipropylene glycol, tripropylene glycol, and higher poly(propylene glycol), such as those having number average molecular weights of from 234 to about 2000 g/mol. In some embodiments, a polyol initiator compound is dipropylene glycol.

In some embodiments, a polyol initiator compound is an alkoxylated derivative of a compound selected from the group consisting of: a diacid, a diol, or a hydroxy acid. In certain embodiments, the alkoxylated derivatives comprise ethoxylated or propoxylated compounds.

In some embodiments, a polyol initiator compound is a polymeric diol. In certain embodiments, a polymeric diol is selected from the group consisting of polyethers, polyesters, hydroxy-terminated polyolefins, polyether-copolyesters, polyether polycarbonates, polycarbonate-copolyesters, polyoxymethylene polymers, and alkoxylated analogs of any of these. In certain embodiments, a polymeric diol has an average molecular weight less than about 2000 g/mol. In some embodiments, a polymeric diol has an average molecular weight of between about 500 g/mol and about 1,500 g/mol. In some embodiments, a polymeric diol has an average molecular weight of between about 750 g/mol and about 1,250 g/mol. In some embodiments, a polymeric diol has an average molecular weight of between about 900 g/mol and about 1,100 g/mol. In some embodiments, a polymeric diol has an average molecular weight of about 1,000 g/mol.

In some embodiments, a polymeric diol is a polyether. In some embodiments, a polymeric diol is polyethylene glycol. In some embodiments, a polymeric diol is polypropylene glycol. In some embodiments, a polymeric diol is a polyester.

In certain embodiments, a polyol initiator compound is a polyhydric alcohol with more than two hydroxy groups. In certain embodiments, a polyol initiator compound is a triol. In certain embodiments, a polyol initiator compound is selected from the group consisting of: glycerol, 1,2,4-butanetriol, 2-(hydroxymethyl)-1,3-propanediol; hexane triols, trimethylol propane, trimethylol ethane, trimethylolhexane, 1,2,4-cyclohexanetrimethanol, pentaerythritol mono esters, pentaerythritol mono ethers, and alkoxylated analogs of any of these. In certain embodiments, such alkoxylated derivatives comprise ethoxylated or propoxylated compounds.

In some embodiments, a polyol initiator compound is an alkoxylated derivative of a trifunctional carboxylic acid or trifunctional hydroxy acid. In certain embodiments, alkoxylated derivatives comprise ethoxylated or propoxylated compounds.

In some embodiments, a polyol initiator compound is a polymeric triol. In some embodiments, the polymeric triol is selected from the group consisting of polyethers, polyesters, hydroxy-terminated polyolefins, polyether-copolyesters, polyether polycarbonates, polyoxymethylene polymers, polycarbonate-copolyesters, and alkoxylated analogs of any of these. In certain embodiments, the alkoxylated polymeric triols comprise ethoxylated or propoxylated compounds.

In some embodiments, a polyol initiator compound is a polyhydric alcohol with four hydroxy groups. In some embodiments, a polyol initiator compound is a tetrol. In some embodiments, a polyol initiator compound is a polyhydric alcohol with more than four hydroxy groups. In some embodiments, a polyol initiator compound is a polyhydric alcohol with six hydroxy groups. In certain embodiments, a polyol initiator compound is dipentaerythritol or an alkoxylated analog or other derivative thereof. In certain embodiments, a polyol initiator compound is sorbitol or an alkoxylated analog thereof.

In some embodiments, a polyol initiator compound is a hydroxy acid. In some embodiments, a polyol initiator compound is an optionally substituted $C_{2-40}$ hydroxy acid. In some embodiments, a polyol initiator compound is a polyester. In certain embodiments, such polyesters have a molecular weight less than about 2000 g/mol.

In certain embodiments, a hydroxy acid is an alpha-hydroxy acid. In certain embodiments, a hydroxy acid is selected from the group consisting of: glycolic acid, DL-lactic acid, D-lactic acid, L-lactic, citric acid, and mandelic acid.

In certain embodiments, a hydroxy acid is a beta-hydroxy acid. In certain embodiments, a hydroxy acid is selected from the group consisting of: 3-hydroxypropionic acid, DL 3-hydroxybutryic acid, D-3 hydroxybutryic acid, L-3-hydroxybutyric acid, DL-3-hydroxy valeric acid, D-3-hydroxy valeric acid, L-3-hydroxy valeric acid, salicylic acid, and derivatives of salicylic acid.

In certain embodiments, a hydroxy acid is a α-ω hydroxy acid. In certain embodiments, a hydroxy acid is selected from the group consisting of: of optionally substituted $C_{3-20}$ aliphatic α-ω hydroxy acids and oligomeric esters.

In certain embodiments, a hydroxy acid is selected from the group consisting of:

In some embodiments, a polyol initiator compound is a polycarboxylic acid. In some embodiments, a polyol initiator compound is a dicarboxylic acid. In some embodiments, a polyol initiator compound is phthalic acid, isophthalic acid, terephthalic acid, maleic acid, succinic acid, malonic acid, glutaric acid, adipic acid, pimelic acid, suberic acid, or azelaic acid.

In some embodiments, a polyol initiator compound is selected from the group consisting of:

In certain embodiments, a polyol initiator compound is derived from a phosphorous-containing molecule. In certain embodiments, a polyol initiator compound has a formula —P(O)(OR)$_k$— where each R is independently an optionally substituted C$_{1-20}$ aliphatic group or an optionally substituted aryl group and k is 0, 1, or 2. In certain embodiments, a polyol initiator compound is a phosphorous-containing molecule selected from the group consisting of:

In certain embodiments, a polyol initiator compound has a formula —P(O)(R)$_k$— where R is an optionally substituted C$_{1-20}$ aliphatic group or an optionally substituted aryl group and k is 0, 1, or 2. In certain embodiments, a polyol initiator compound is a phosphorous-containing molecule selected from the group consisting of:

where each of R is as defined above and in the classes and subclasses herein;

$R^d$ is optionally substituted $C_{1-6}$ aliphatic; and
z is 2-30.

In certain embodiments, a polyol initiator compound has a formula —PR— where R is an optionally substituted $C_{1-20}$ aliphatic group or an optionally substituted aryl group.

In certain embodiments, the methods of drying a polyol initiator compound further comprise the step of decreasing viscosity of a polyol initiator compound. In some embodiments, the step of decreasing viscosity comprises increasing temperature of a polyol initiator compound (e.g., within a range of about 50° C. to about 100° C.). In some embodiments, a temperature a polyol initiator compound is increased prior to and/or during the step of contacting a polyol initiator compound with one or more molecular sieves.

C. Flow Rates

In some embodiments, a composition comprising the polyol initiator compound flows through a vessel containing a molecular sieve. In some embodiments, a composition comprising the polyol initiator compound flows through a vessel containing a molecular sieve at a flow rate of about 0.1 to about 10.0 mL/min. In some embodiments, a composition comprising the polyol initiator compound flows through a vessel containing a molecular sieve at a flow rate of about 0.1 to about 5.0 mL/min. In some embodiments, a composition comprising the polyol initiator compound flows through a vessel containing a molecular sieve at a flow rate of about 0.25 to about 5.0 mL/min. In some embodiments, a composition comprising the polyol initiator compound flows through a vessel containing a molecular sieve at a flow rate of about 0.5 to about 5.0 mL/min. In some embodiments, a composition comprising the polyol initiator compound flows through a vessel containing a molecular sieve at a flow rate of about 1.0 to about 5.0 mL/min. In some embodiments, a composition comprising the polyol initiator compound flows through a vessel containing a molecular sieve at a flow rate of about 2.0 to about 5.0 mL/min. In some embodiments, a composition comprising the polyol initiator compound flows through a vessel containing a molecular sieve at a flow rate of about 2.5 to about 5.0 mL/min. In some embodiments, a composition comprising the polyol initiator compound flows through a vessel containing a molecular sieve at a flow rate of about 5.0 to about 10.0 mL/min. In some embodiments, a composition comprising the polyol initiator compound flows through a vessel containing a molecular sieve at a flow rate of about 0.1 to about 4.0 mL/min. In some embodiments, a composition comprising the polyol initiator compound flows through a vessel containing a molecular sieve at a flow rate of about 0.1 to about 3.0 mL/min. In some embodiments, a composition comprising the polyol initiator compound flows through a vessel containing a molecular sieve at a flow rate of about 0.1 to about 2.0 mL/min. In some embodiments, a composition comprising the polyol initiator compound flows through a vessel containing a molecular sieve at a flow rate of about 0.1 to about 1.0 mL/min. In some embodiments, a composition comprising the polyol initiator compound flows through a vessel containing a molecular sieve at a flow rate of about 0.1 to about 0.5 mL/min. In some embodiments, a composition comprising the polyol initiator compound flows through a vessel containing a molecular sieve at a flow rate of about 0.25 to about 4.0 mL/min. In some embodiments, a composition comprising the polyol initiator compound flows through a vessel containing a molecular sieve at a flow rate of about 0.25 to about 3.0 mL/min. In some embodiments, a composition comprising the polyol initiator compound flows through a vessel containing a molecular sieve at a flow rate of about 0.5 to about 2.5 mL/min. In some embodiments, a composition comprising the polyol initiator compound flows through a vessel containing a molecular sieve at a flow rate of about 0.5 to about 3.0 mL/min. In some embodiments, a composition comprising the polyol initiator compound flows through a vessel containing a molecular sieve at a flow rate of about 0.5 to about 5.0 mL/min.

D. Moisture Content

In some embodiments, after contacting a composition comprising a polyol initiator compound with a molecular sieve, the resulting compositions comprises less water as measured by Karl-Fisher titration, as compared to the composition comprising a polyol initiator compound before contacting the molecular sieve.

In some embodiments, after contacting a composition comprising a polyol initiator compound with a molecular sieve, the resulting compositions comprises less than 200 ppm water as measured by Karl-Fisher titration. In some embodiments, after contacting a composition comprising a polyol initiator compound with a molecular sieve, the resulting compositions comprise less than 150 ppm water as measured by Karl-Fisher titration. In some embodiments, after contacting a composition comprising a polyol initiator compound with a molecular sieve, the resulting compositions comprise less than 125 ppm water as measured by Karl-Fisher titration. In some embodiments, after contacting a composition comprising a polyol initiator compound with a molecular sieve, the resulting compositions comprise less than 115 ppm water as measured by Karl-Fisher titration. In some embodiments, after contacting a composition comprising a polyol initiator compound with a molecular sieve, the resulting compositions comprise less than 100 ppm water as measured by Karl-Fisher titration.

In some embodiments, after contacting a composition comprising a polyol initiator compound with a molecular sieve, the resulting compositions comprise between about 25 ppm and about 150 water as measured by Karl-Fisher titration. In some embodiments, after contacting a composition comprising a polyol initiator compound with a molecular sieve, the resulting compositions comprise between about 25 ppm and about 125 water as measured by Karl-Fisher titration. In some embodiments, after contacting a composition comprising a polyol initiator compound with a molecular sieve, the resulting compositions comprise between about 50 ppm and about 100 water as measured by Karl-Fisher titration.

II. Systems

In some embodiments, the present invention provides systems for drying a polyol initiator compound. Accordingly, in some embodiments, the present invention provides a systems comprising:
  a vessel comprising one or more molecular sieves; and
  a polyol initiator input subsystem fluidly connected to the vessel, wherein a composition comprising a polyol initiator compound flows into the vessel through the polyol initiator input subsystem.

In some embodiments, a molecular sieve is as described above within the "Methods" section (e.g., section I-A). In some embodiments, a polyol initiator compound is as described above within the "Methods" section (e.g., section I-B). In some embodiments, the composition flows through the vessel at a flow rate as described above within the "Methods" section (e.g., section I-C). In some embodiments, after flowing through the vessel, the moisture content of the resulting composition is as described above within the "Methods" section (e.g., section I-D).

Figure 1:
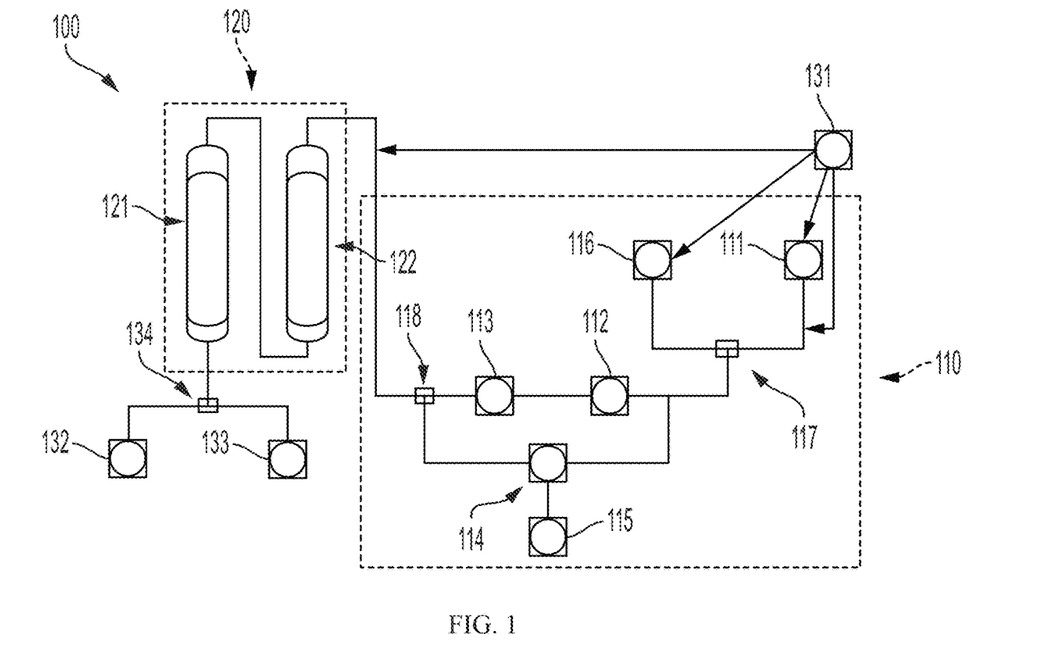
FIG. 1 is a process flow diagram for an exemplary system for drying a polyol initiator compound.

FIG. 1 is a process flow diagram for exemplary system 100, the system of an illustrative embodiment of the systems and methods disclosed herein. For example, as seen in FIG. 1, a system 100 comprises: a polyol initiator input subsystem 110, a drying subsystem 120, and a receiver tank 132. Polyol initiator input subsystem 110 is fluidly connected to drying subsystem 120, where a composition comprising a polyol initiator compound flows from polyol initiator input subsystem 110 to drying subsystem 120. Polyol initiator input subsystem 110 is upstream of drying subsystem 120. Drying subsystem 120 is then fluidly connected to receiver tank 132, wherein a composition comprising a polyol initiator compound flows from drying subsystem 120 to receiver tank 132. Drying subsystem 120 is upstream of receiver tank 132. In some embodiments, receiver tank 132 comprises a ventilation point. In some embodiments, as also seen in FIG. 1, drying subsystem 120 is also fluidly connected to sampling vessel 133, where samples of a composition comprising a polyol initiator compound may be collected and, e.g., the moisture content may be measured, e.g., by Karl Fisher titration. In some embodiments, a control valve 134 is configured to receive a signal from a detector or another source (e.g., a signal received from a terminal operated by a human). A signal sent to control valve 134 will cause the composition comprising a polyol initiator compound to flow into receiver tank 132 and/or sampling vessel 133.

Figure 2:
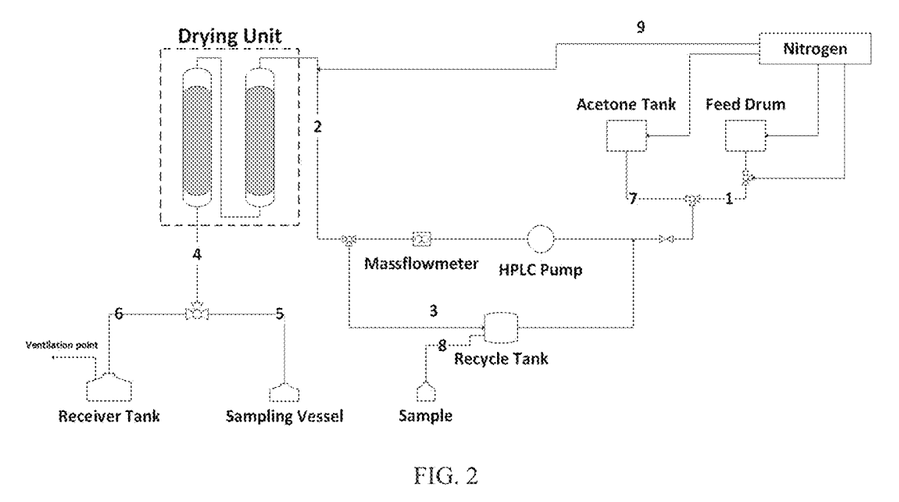
FIG. 2 is an exemplary process flow diagram for drying a polyol initiator compound.

In some embodiments, as also seen in FIG. 1, polyol initiator input subsystem 110 comprises feed drum 111, which stores a composition comprising a polyol initiator compound. In some embodiments, as also seen in FIG. 1, feed drum 111 is fluidly connected to pump 112 (e.g., an HPLC pump as shown in FIG. 2) and flow meter 113 (e.g., a volumetric flow meter or a mass flow meter as shown in FIG. 2). Pump 112 is configured to pump a composition comprising a polyol initiator compound from feed drum 111 to flow meter 113, where the flow rate may be configured (e.g., to the flow rates described above and herein). Feed drum 111 is upstream of pump 112 and flow meter 113.

In some embodiments, as also seen in FIG. 1, feed drum 111 is fluidly connected to drying subsystem 120 and recycling tank 114, e.g., through pump 112 and flow meter 113. In some embodiments, as also seen in FIG. 1, polyol initiator input subsystem 110 comprises control valve 118. In some embodiments, control valve 118 is configured to receive a signal from a detector or another source (e.g., a signal received from a terminal operated by a human). A signal sent to control valve 118 will cause the composition comprising a polyol initiator compound to flow into drying unit 120 and/or recycling tank 114. In some embodiments, as also seen in FIG. 1, recycling tank 114 is fluidly connected to sampling vessel 115, whereby the contents may be sampled, tested, and monitored (e.g., temperature, moisture content, etc.). Recycling tank 114 also connects back to drying subsystem 120, whereby the composition continuously flows in and out of recycling tank 114 until control valve 118 is configured to allow flow to drying subsystem 120. Recycling tank 114 is upstream of drying unit 120.

In some embodiments, as also seen in FIG. 1, polyol initiator input subsystem 110 comprises flushing vessel 116. In some embodiments, flushing vessel 116 comprises a volatile solvent (e.g., acetone as shown in FIG. 2). In some embodiments, flushing vessel 116 is fluidly connected to control valve 117. Flushing vessel 116 is upstream of valve 117. In some embodiments, control valve 117 is configured to receive a signal from a detector or another source (e.g., a signal received from a terminal operated by a human). A signal sent to control valve 117 will cause the contents of either flushing vessel 116 or feed drum 111 to flow through polyol initiator subsystem 110. Flushing vessel 116 flows through polyol initiator input subsystem 110 similarly as described for feed drum 111.

In some embodiments, as also seen in FIG. 1, system 100 further comprises flushing vessel 131. In some embodiments, flushing vessel 131 comprises a dry inert gas (e.g., nitrogen gas as shown in FIG. 2). In some embodiments, flushing vessel 131 is fluidly connected to drying subsystem 120 and/or polyol initiator subsystem 110, whereby flushing vessel 131 flows a dry inert gas (e.g., nitrogen gas) through drying subsystem 120 and/or polyol initiator subsystem 110 to ensure no moisturized air in drying subsystem 120 and/or polyol initiator subsystem 110. In some embodiments, as also seen in FIG. 1, flushing vessel 131 is fluidly connected to feed drum 111, flushing vessel 116, or at other points within polyol initiator subsystem 110. In some embodiments, as also seen in FIG. 1, flushing vessel 131 is fluidly connected to drying subsystem 120. Flushing vessel 131 is upstream of feed drum 111, flushing vessel 116, other points within polyol initiator subsystem 110, and/or drying subsystem 120.

In some embodiments, as also seen in FIG. 1, drying subsystem 120 comprises vessel 121 and/or vessel 122. In some embodiments, vessels 121 and/or vessel 122 is a column comprising molecular sieves. In some embodiments, vessels 121 and/or vessel 122 further comprising packing material, e.g., glass wool. In some embodiments, vessels 121 and/or vessel 122 comprise a bed reactor, which comprises molecular sieves and/or packing material (e.g., glass wool). In some embodiments, molecular sieves are randomly packed in vessels 121 and/or vessel 122. In some embodiments, molecular sieves are stacked or arranged in vessels 121 and/or vessel 122. In some embodiments, packing density of molecular sieves in vessels 121 and/or vessel 122 is within a range of about 0.1 to about 0.7. In some embodiments, packing density of molecular sieves in vessel 121 is substantially constant within vessel 121. In some embodiments, packing density of molecular sieves in vessel 121 increases in the direction of flow of the polyol initiator compound. In some embodiments, packing density of molecular sieves in vessel 121 decreases in the direction of flow of the polyol initiator compound. In some embodiments, packing density of molecular sieves in vessel 122 is substantially constant within vessel 122. In some embodiments, packing density of molecular sieves in vessel 122 increases in the direction of flow of the polyol initiator compound. In some embodiments, packing density of molecular sieves in vessel 122 decreases in the direction of flow of the polyol initiator compound. In some embodiments, packing density of molecular sieves in vessel 121 and packing density of molecular sieves in vessel 122 are substantially same. In some embodiments, packing density of molecular sieves in vessel 121 and packing density of molecular sieves in vessel 122 are substantially different.

In some embodiments, drying subsystem 120 is configured to monitor the temperature. In some embodiments, drying subsystem 120 is configured to maintain an elevated temperature before a composition comprising a polyol initiator compound is flowing through. For example, in some embodiments, drying subsystem 120 is configured to maintain a temperature above about 100° C., above about 200° C., above about 250° C., above about 280° C., above about 300° C., or above about 400° C. before a composition comprising a polyol initiator compound is flowing through. In some embodiments, drying subsystem 120 is configured to maintain a temperature between about 200° C. and about 400° C., between about 250° C. and about 350° C., or between about 280° C. and about 300° C. before a composition comprising a polyol initiator compound is flowing through. In some embodiments, drying subsystem 120 is configured to maintain any of the temperatures listed above and herein for at least 1 hr, at least 2 hrs, or at least 3 hrs. In some embodiments, drying subsystem 120 is configured to maintain any of the temperatures listed above and herein for between about 1 hr and about 5 hrs, between about 2 hrs and about 4 hrs, or between about 2.5 hrs and about 3.5 hrs. In some embodiments, drying subsystem 120 is configured to maintain any of the temperatures listed above and herein for about 1 hr, 2, hrs, 3, hrs, 4 hr, or 5 hrs.

In some embodiments, dry system 120 is also configured to, after maintaining at an elevated temperature (e.g., as described in the prior paragraph), to be maintained at a lower temperature when a composition comprising a polyol initiator compound is flowing through. For example, in some embodiments, dry system 120 is to maintain a temperature between about 20° C. and about 200° C., between about 30° C. and about 150° C., between about 30° C. and about 120° C., between about 40° C. and about 110° C., between about 50° C. and about 100° C., between about 50° C. and about 100° C., or between about 50° C. and about 75° C., while a composition comprising a polyol initiator compound flows through.

In some embodiments, FIG. 2 is an exemplary process flow diagram of FIG. 1.

EXAMPLES

The present invention is illustrated by the following examples. It is to be understood that the particular examples, materials, amounts, and procedures are to be interpreted broadly in accordance with the scope and spirit of the invention as set forth herein.

Example 1: Process for Drying Polypropylene Glycol (PPG)

A system (e.g., as depicted in FIG. 1 and FIG. 2) was used to removed water from PPG. Approximately 1.0 L of untreated PPG, with a moisture content of about 3,000 ppm, was loaded into the feed drum (max volume 5.0 L). A small amount of nitrogen (0.1 L/min) was purged in the feed drum to ensure no moisturized air in the system.

Figure 3:
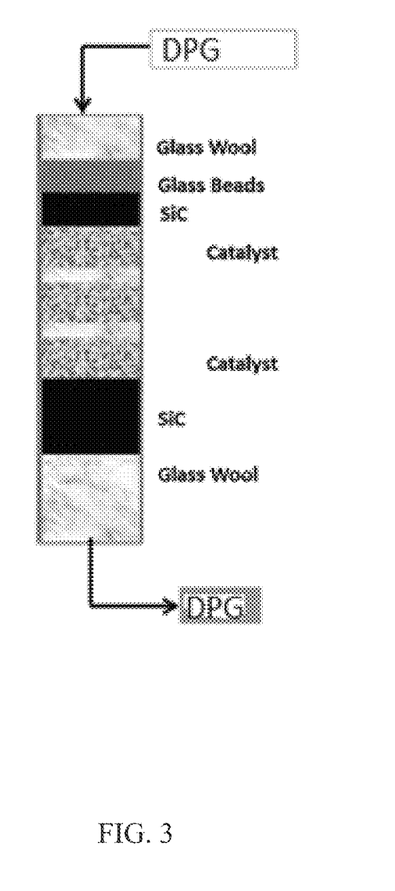
FIG. 3 is an exemplary bed reactor of a drying column, packed with glass wool.

Both drying columns (total volume of about 55 mL) were prepared by inserting an about 3.0 cm layer of glass wool into the bed reactor of the drying columns until it was touching the bottom holder of the mesh bed reactor, e.g., as depicted in FIG. 3. Each bed reactor was filled with molecular sieve beads (pore size of 3 angstroms, 36.0 g) and capped with another 3.0 cm layer of glass wool. The bed reactors were tightly secured and placed back in the drying columns. The drying columns were continuously purged with nitrogen (0.1 L/min) while raising the temperature of both columns to 280-300° C. for 3.0 hrs in order to activate the molecular sieves.

After the activation step is completed, the drying columns were cooled down to the desired temperature (e.g., 50-100° C.) and kept at this temperature for 1.0 h under constant nitrogen flow. When the drying columned reached the set temperature of 50-100° C., the PPG was pumped, using an HPLC pump, at a flow rate in the rage of 0.5-2.5 mL/min. Prior to collecting the purified PPG, both the sampling and product valves were opened for 5.0 min to flush the first outcome coming from the bed reactor, which typically occurred after 20.0 min from pumping the liquid began. The sample was collected with an interval of 1.0 h in a sealed glass vial and the moisture level was tested using Karl-Fisher titration.

Table 1 depicts the effects of flowrate and temperature on the removal of water from PPG, and demonstrates that the disclosed processes and systems reduced water content below 200 ppm, and in some cases, below 100 ppm.

TABLE 1

Moisture Level Content for PPG at Different Temperatures and Flowrates

| Temperature (° C.) | Flowrate, Q (mL/min) | Moisture level (ppm) |
| --- | --- | --- |
| 50 | 2.5 | 192 |
| 75 | 0.5 | 99 |
| 100 | 2.5 | 135 |
| 100 | 1.25 | 88 |

Example 2: Process for Drying Dipropyleneglycol (DPG)

DPG was dried as described in Example 1. Table 2 depicts the effects of flowrate and temperature on the removal of water from DPG, and demonstrates that the disclosed processes and systems reduced water content below 200 ppm, and in some cases, below 100 ppm.

| Temperature (° C.) | Flowrate, Q (mL/min) | Moisture level (ppm) |
| --- | --- | --- |
| 30 | 0.5 | 230 |
| 50 | 0.5 | 70 |
| 50 | 5 | 84 |
| 50 | 10 | 112 |

EQUIVALENTS

All material cited in this application, including, but not limited to, patents and patent applications, regardless of the format of such literature and similar materials, are expressly incorporated herein by reference in their entirety. In the event that one or more of the incorporated literature and similar materials differs from or contradicts this application, including but not limited to defined terms, term usage, described techniques, or the like, this application controls.

The invention claimed is:

1. A method of drying a polyol initiator compound, the method comprising the step of:
   flowing a composition comprising a polyol initiator compound through a vessel at a flow rate of about 0.5 to about 2.5 mL/min; and
   contacting the composition comprising the polyol initiator compound with one or more molecular sieves,
   wherein the vessel contains the molecular sieves and wherein the molecular sieves are maintained at a temperature between about 50° C. and about 100° C. while in contact with the polyol initiator compound.

2. The method of claim 1, wherein the molecular sieves are crystalline potassium aluminosilicate molecular sieve beads.

3. The method of claim 1, wherein the molecular sieves have a pore size of about 3 angstroms.

4. The method of claim 1, wherein the polyol initiator compound is selected from the group consisting of di propylene glycol, polypropylene glycol, ethylene glycol, 1,2-propylene glycol, glycerol, ethoxylated glycerol, ethylene diamine, N-methyl-amino-dipropylamine, pentacrythriol, sorbitol, and sucrose.

5. The method of claim 1, wherein the polyol initiator compound selected from the group consisting of di propylene glycol and polypropylene glycol.

6. The method of claim 1, wherein, after contacting a composition comprising a polyol initiator compound with one or more molecular sieves, the resulting composition comprises less than 120 ppm of water as measured by Karl-Fisher titration.

7. The method of claim 1, wherein the molecular sieves are activated.

\* \* \* \* \*